(12) United States Patent
Weststrate et al.

(10) Patent No.: US 6,997,900 B2
(45) Date of Patent: Feb. 14, 2006

(54) CONNECTOR FOR USE WITH A MEDICAL CATHETER AND MEDICAL CATHETER ASSEMBLY

(75) Inventors: Patrice A. Weststrate, Norwood, MA (US); John C. Holmes, Chepachet, RI (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/315,396

(22) Filed: Dec. 9, 2002

(65) Prior Publication Data

US 2004/0111056 A1 Jun. 10, 2004

(51) Int. Cl.
*A61M 29/00* (2006.01)

(52) U.S. Cl. .................. 604/104; 604/910; 604/533

(58) Field of Classification Search ............. 604/264, 604/103.03, 174, 175, 910, 516, 104, 523, 604/533–535
See application file for complete search history.

(56) References Cited

U.S. PATENT DOCUMENTS

| | | | |
|---|---|---|---|
| 3,884,242 A * | 5/1975 | Bazell et al. | 128/207.15 |
| 4,144,889 A * | 3/1979 | Tyers et al. | 607/130 |
| 4,758,219 A | 7/1988 | Sacks et al. | |
| 4,861,334 A | 8/1989 | Nawaz | |
| 4,900,306 A | 2/1990 | Quinn et al. | |
| 5,112,310 A | 5/1992 | Grobe | |
| 5,167,627 A * | 12/1992 | Clegg et al. | 604/103.03 |
| 5,391,159 A | 2/1995 | Hirsch et al. | |
| 6,315,789 B1 * | 11/2001 | Cragg | 606/232 |

* cited by examiner

*Primary Examiner*—LoAn H. Thanh
(74) *Attorney, Agent, or Firm*—Kriegsman & Kriegsman

(57) ABSTRACT

Connector for use with a medical catheter assembly and medical catheter assembly including the connector. In one embodiment, the connector comprises a rear portion, an intermediate portion, and a front portion. The rear portion is frusto-conical in shape and tapers rearwardly in cross-sectional diameter from its front end. A centrally-disposed, smaller-diameter, longitudinal bore is provided in the rear portion, the bore being appropriately dimensioned to receive a guidewire therethrough. The intermediate portion is generally cylindrical and is shaped to include a centrally-disposed, larger-diameter longitudinal bore and a pair of longitudinally-extending slots providing access to the larger-diameter bore. The front portion is frusto-conical in shape and tapers forwardly in cross-sectional diameter from its rear end. In use, a silicone tube is inserted into the larger-diameter bore of the intermediate portion, and the rear and intermediate portions of the connector are inserted into a gastrostomy feeding tube. A silicone glue is then used to bond the silicone tube to the gastrostomy feeding tube. The front end of the connector is inserted into a dilator and is secured thereto by spin-welding.

9 Claims, 12 Drawing Sheets

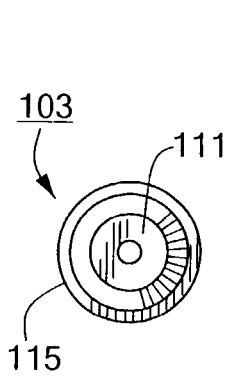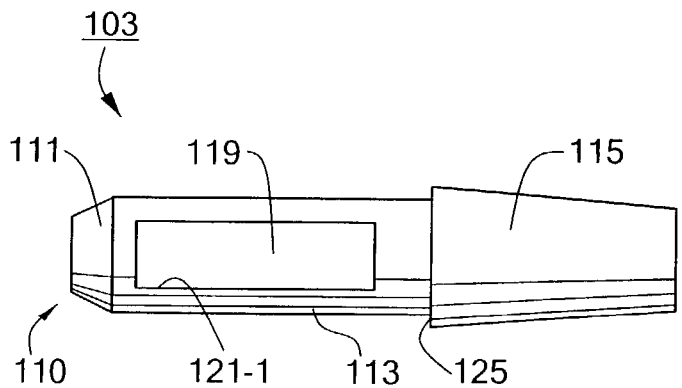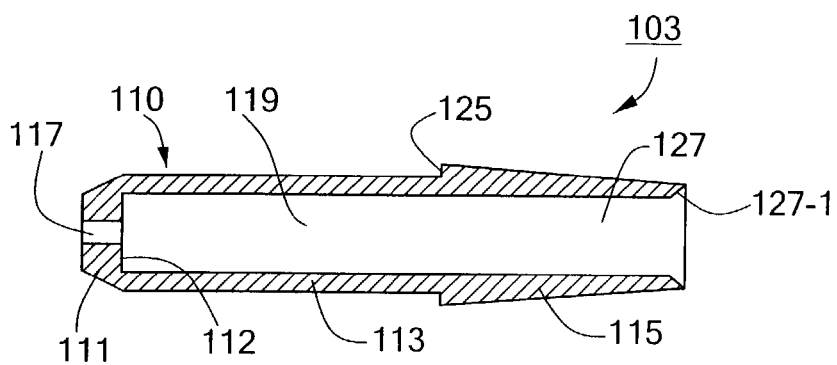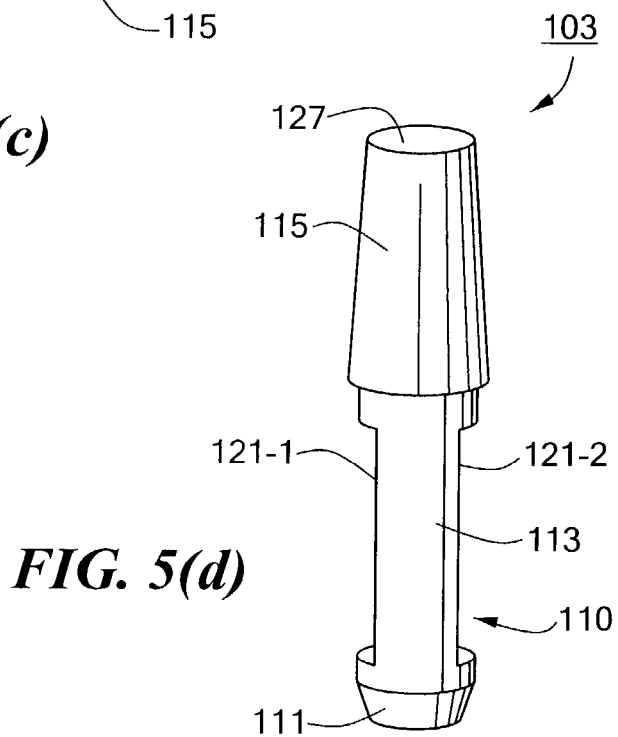
FIG. 5(a)
FIG. 5(b)
FIG. 5(c)
FIG. 5(d)

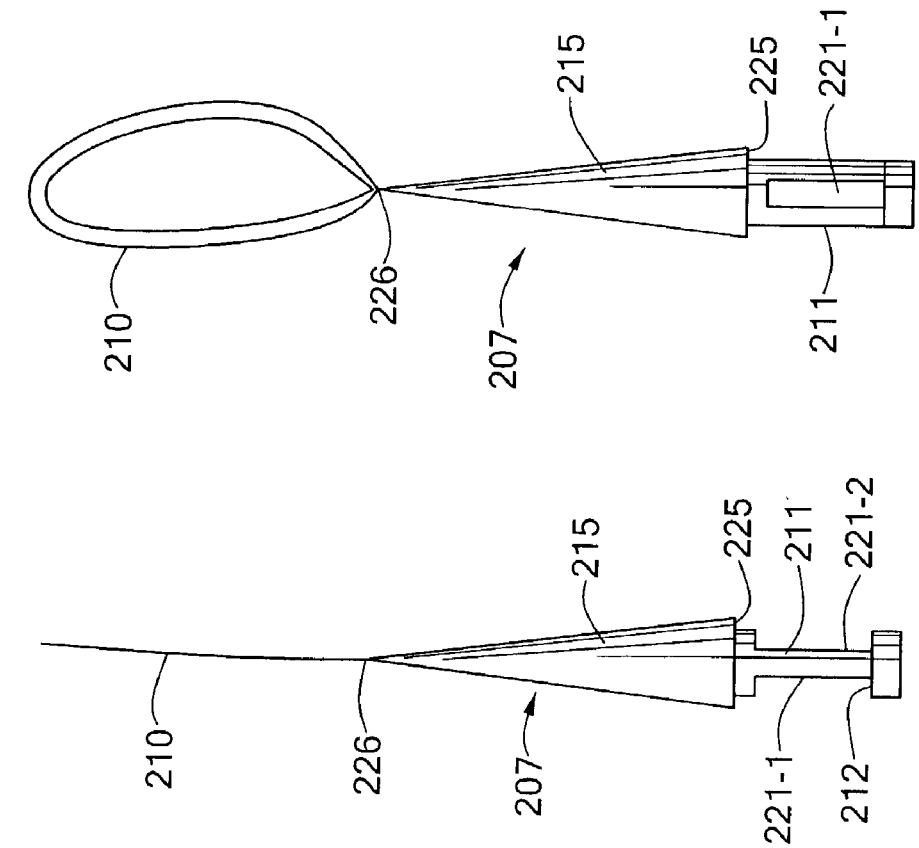
*FIG. 7(d)*
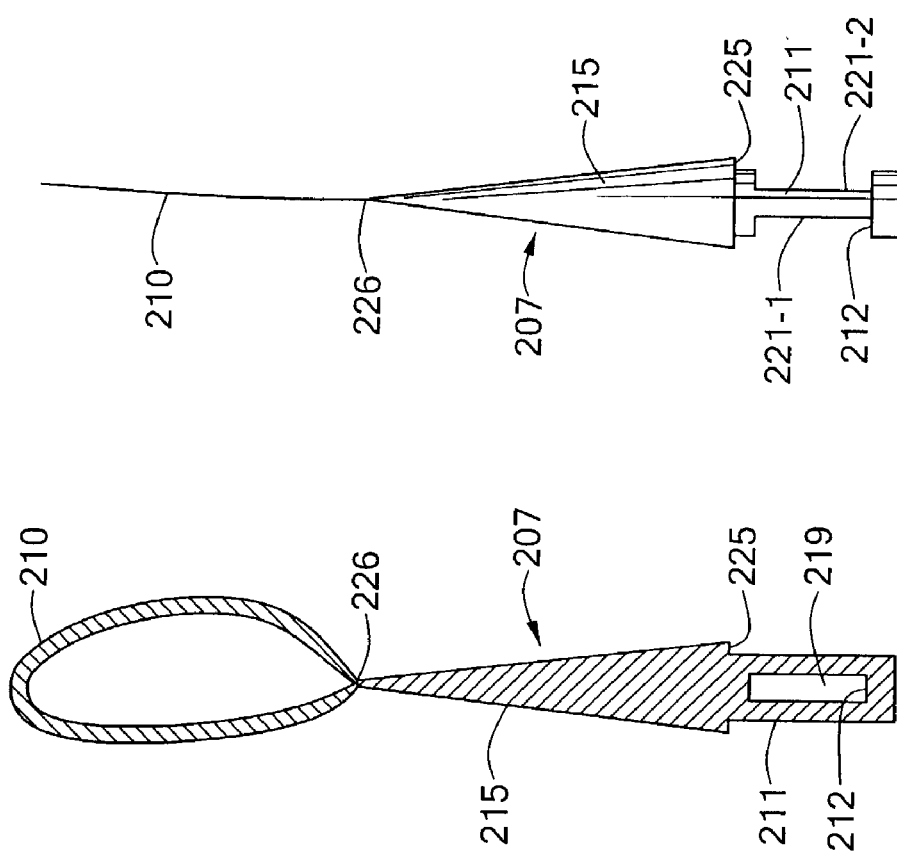
*FIG. 7(c)*
*FIG. 7(b)*
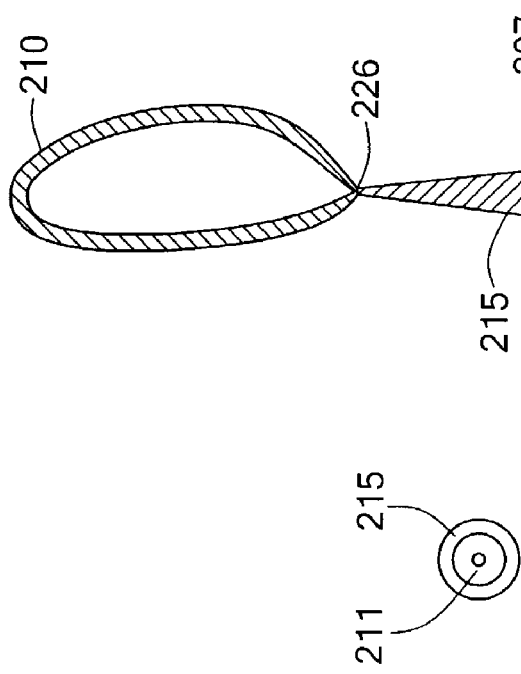
*FIG. 7(a)*

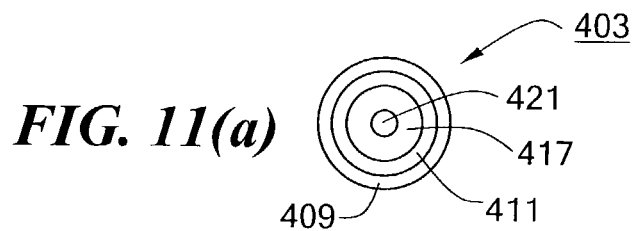
*FIG. 11(a)*
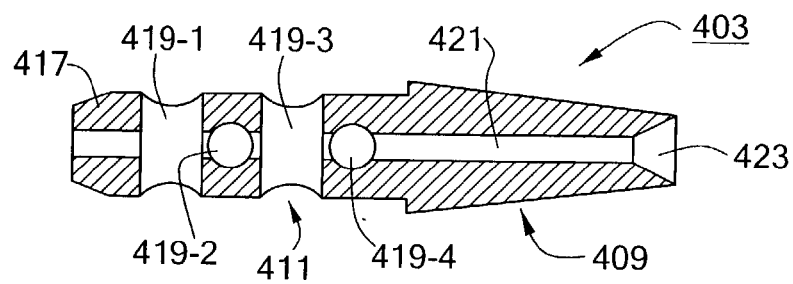
*FIG. 11(b)*
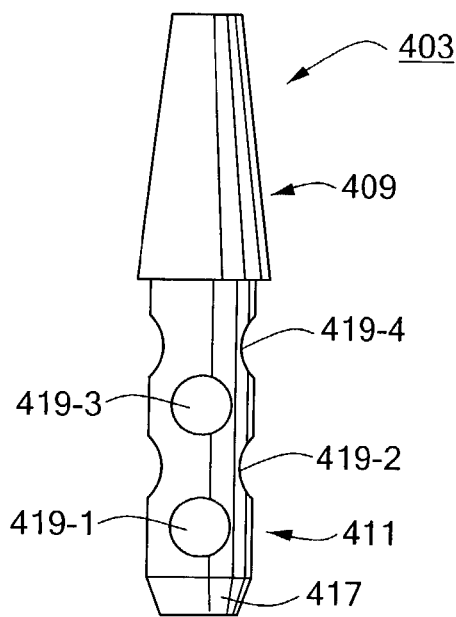 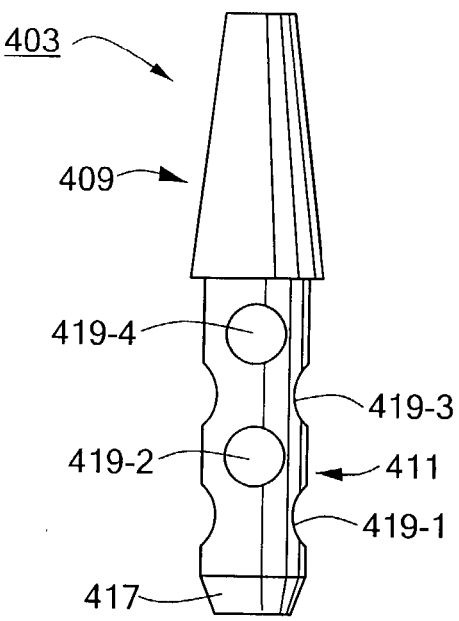
*FIG. 11(c)*  *FIG. 11(d)*

CONNECTOR FOR USE WITH A MEDICAL CATHETER AND MEDICAL CATHETER ASSEMBLY

BACKGROUND OF THE INVENTION

The present invention relates generally to medical catheters, such as gastrostomy feeding tubes, and relates more particularly to medical catheter assemblies, such as percutaneous endoscopic gastrostomy (PEG) devices.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a catheter or feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy and result in the implantation of a catheter/bolster assembly (also commonly referred to as a percutaneous endoscopic gastrostomy (PEG) device) in the patient. Two of the more common techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to the push method, the distal end of an endoscope is inserted into a patient's mouth and is passed through the esophagus into the stomach. After distension of the stomach by inflation, an entry site on the abdomen is identified, and an incision is made by passing a needle with an outer cannula (e.g., a Seldinger needle) through the abdominal wall and into the stomach. The needle is then removed while keeping the cannula in place. Next, a snare is inserted into the stomach via the endoscope and is looped over the distal end of the cannula. A first end of a flexible guidewire is then passed through the cannula and into the stomach where it is grasped by the snare, the second end of the guidewire remaining external to the patient. The endoscope and the snare are then withdrawn from the mouth of the patient to deliver the first end of the guidewire.

A catheter assembly is then inserted over the first end of the guidewire and is pushed over the guidewire towards its second end. The catheter assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster (also referred to collectively as a "PEG device") are typically made of a soft, biocompatible material, like silicone rubber, and may form a unitary structure. The dilator, which tapers in outer diameter from its trailing end to its leading end, is typically made of polyethylene or a like material which is stiffer than silicone but which still possesses some flexibility. Advancement of the catheter assembly over the guidewire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the gastric wall.

With the internal bolster in place against the gastric wall, a proximal portion of the implanted gastrostomy feeding tube is then typically cut and removed from the implanted tube to reduce the externally-extending portion of the tube to a desired length. An external bolster is typically secured to the remaining implanted portion of the feeding tube to engage the abdomen in such a way as to prevent longitudinal movement of the feeding tube within the stoma tract. Additionally, a "Y-port" adapter is typically attached to the proximal end of the implanted feeding tube, the Y-port adapter being adapted to receive a pair of connector tips through which food and/or medications may be dispensed. In addition, a detachable locking clip is typically secured to the implanted feeding tube at a point between the external bolster and the Y-port adapter to prevent gastric fluids from escaping through the proximal end of the feeding tube when the feeding tube is not in use.

As can readily be appreciated, because the leading end of the gastrostomy feeding tube is drawn through the abdomen by pulling on the dilator, the connection between the dilator and the gastrostomy feeding tube must be strong enough to withstand the tensile force applied thereto. Otherwise, the gastrostomy feeding tube may separate from the dilator prior to emergence of the feeding tube from the patient, thereby requiring the feeding tube to be retrieved from the patient and possibly leading to undesired complications. For PEG assembly connections, such as the aforementioned connection between the gastrostomy feeding tube and the dilator, the industry standard minimum tensile strength is 17 pounds (see BS EN 1615:2000).

Historically, however, this standard has not typically been met by the conventional type of connection used to couple a dilator to a gastrostomy feeding tube. An example of such a connection typically comprises an appropriately dimensioned tubular fitting having barbs at opposite ends thereof. One end of the tubular fitting is inserted into the trailing end of the dilator, and the opposite end of the fitting is inserted into the leading end of the gastrostomy feeding tube. The connection also comprises a short length of plastic tubing, which is shrink-wrapped around the trailing end of the dilator and the leading end of the feeding tube (as well as surrounding the fitting disposed within the trailing end of the dilator and the leading end of the feeding tube).

In addition to failing frequently to meet the minimum tensile strength required for a connection between a dilator and a feeding tube, other shortcomings with the above-described connection are (i) that the application of the shrink-wrapped length of tubing to the assembly requires the expenditure of time and labor, (ii) that the shrink-wrapped tubing undesirably increases the cross-sectional profile of the assembly, and (iii) that there is a perception that the ends of the shrink-wrapped tubing, which ends do not lie flush with the dilator or the feeding tube, may snag tissue as the assembly makes its winding path through the patient.

According to the pull method, the distal end of an endoscope is inserted into a patient's mouth and is passed through the esophagus into the stomach. After distension of the stomach by inflation, an entry site on the abdomen is identified, and an incision is made by passing a needle with an outer cannula (e.g., a Seldinger needle) through the abdominal wall and into the stomach. The needle is then removed while keeping the cannula in place. Next, a snare is inserted into the stomach via the endoscope and is looped over the distal end of the cannula. A first end of a suture is then passed through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a catheter assembly, the catheter assembly comprising a gastrostomy feeding tube having an internal bolster at its trailing end and a plastic fitting at its leading end. The plastic fitting has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop.

Using the second end of the suture, the catheter assembly is then pulled retrograde through the patient until the gastrostomy feeding tube emerges from the abdomen of the patient and the internal bolster engages the gastric wall of the patient. Next, as is the case in the push method, the implanted gastrostomy feeding tube is typically cut to a desired length, an external bolster is typically secured to the cut implanted tube, a "Y-port" adapter is typically attached to the proximal end of the implanted feeding tube, and a detachable locking clip is typically secured to the implanted feeding tube at a point between the external bolster and the Y-port adapter.

As can readily be appreciated, because the catheter assembly is moved into position within the patient's body by pulling on the suture, it is very important that the plastic fitting maintain its coupling to the gastrostomy feeding tube.

SUMMARY OF THE INVENTION

It is an object of the present invention to provide a novel medical catheter assembly.

It is another object of the present invention to provide a medical catheter assembly as described above that overcomes at least some of the problems described above in connection with existing medical catheter assemblies of the type used to implant PEG devices.

The present invention is based, at least in part, on the present inventors' recognition that many PEG-implanting assemblies in existence prior to the release of the BS EN 1615:2000 industry standards fail to withstand the considerable separation force applied during implantation, which is attributable, in large part, to the fact that a strong connection cannot be maintained between a gastrostomy feeding tube, which is typically made of silicone rubber, and a connector, fitting or dilator inserted thereinto, said connector, fitting or dilator typically not being made of silicone rubber.

Therefore, according to one aspect of the invention, there is provided a connector adapted for use in connecting a first length of tubing to a second length of tubing, said second length of tubing being made of a silicone rubber, said connector being a unitary structure comprising a front portion and a rear portion, said front portion being adapted for insertion into said first length of tubing, said rear portion being adapted for insertion into said second length of tubing, said front portion being frusto-conical and tapering forwardly in cross-sectional diameter, said front portion having a first longitudinal bore, said rear portion having a forward section and a rearward section, said forward section being generally cylindrical and having a second longitudinal bore and a pair of slots providing side access to said second longitudinal bore, said second longitudinal bore being coaxial with and equal in diameter to said first longitudinal bore, said rearward section having a third longitudinal bore, said third longitudinal bore being coaxial with and smaller in diameter than said first longitudinal bore.

According to another aspect of the invention, there is provided a connector adapted for use in connecting a first length of tubing to a second length of tubing, said second length of tubing being made of a silicone rubber, said connector being a unitary structure having a longitudinal bore and comprising a front portion and a rear portion, said front portion being adapted for insertion into said first length of tubing, said rear portion being adapted for insertion into said second length of tubing, said front portion being frusto-conical and tapering forwardly in cross-sectional diameter, said rear portion having a first transversely-extending opening and a second transversely-extending opening, said first and second transversely-extending openings being adapted to receive a quantity of a silicone glue, said second transversely-extending opening extending orthogonally relative to said first transversely-extending opening.

According to yet another aspect of the invention, there is provided a fitting assembly adapted for connection to a length of tubing, the length of tubing being made of a silicone rubber, said fitting assembly comprising (i) a fitting, said fitting being a unitary structure comprising a front portion and a rear portion, said front portion being conical in shape and tapering forwardly in cross-sectional diameter, said rear portion being adapted for insertion into the length of tubing, said rear portion having a forward section and a rearward section, said forward section being generally cylindrical and having a longitudinal bore and a pair of slots providing side access to said longitudinal bore; and (ii) a wire loop, said wire loop being secured to said front portion of said fitting and extending forwardly therefrom.

According to still yet another aspect of the invention, there is provided a fitting assembly adapted for connection to a length of tubing, said length of tubing being made of a silicone rubber, said fitting assembly comprising (i) a fitting, said fitting being a unitary structure comprising a front portion and a rear portion, said front portion being conical and tapering forwardly in cross-sectional diameter, said rear portion being adapted for insertion into said length of tubing and having a first transversely-extending opening and a second transversely-extending opening, said first and second transversely-extending openings being adapted to receive a quantity of a silicone glue, said second transversely-extending opening extending orthogonally relative to said first transversely-extending opening; and (ii) a wire loop, said wire loop being secured to said front portion of said fitting and extending forwardly therefrom.

According to a further aspect of the invention, there is provided a medical catheter assembly, said medical catheter assembly comprising: (a) a medical catheter, said medical catheter being made of silicone rubber and having a proximal end, a distal end and a longitudinal bore; (b) an internal bolster, said internal bolster being disposed at said distal end of said medical catheter; (c) a connector, said connector being an elongated member having a front portion, a rear portion, and a longitudinal bore, said rear portion having at least one slot providing side access to said longitudinal bore, said rear portion of said connector being disposed within said proximal end of said medical catheter; (d) a length of tubing, said length of tubing being disposed within said longitudinal bore of said connector and being exposed through said at least one slot, said length of tubing being made of silicone rubber; and (e) a silicone rubber glue, said silicone rubber glue being sandwiched between an exposed portion of said length of tubing and said medical catheter for bonding said length of tubing to said medical catheter.

According to yet a further aspect of the invention, there is provided a medical catheter assembly, said medical catheter assembly comprising (a) a medical catheter, said medical catheter being made of silicone rubber and having a proximal end, a distal end and a longitudinal bore; (b) an internal bolster, said internal bolster being disposed at said distal end of said medical catheter; and (c) a fitting assembly, said fitting assembly comprising (i) a fitting, said fitting including a front portion and a rear portion, said front portion being shaped to serve as a dilator, said rear portion being disposed within said proximal end of said medical catheter and being shaped to include a longitudinally-extending bore and at least one slot providing side access to said longitudinally-extending bore, (ii) a length of tubing, said length of tubing being disposed within said longitudinally-extending bore of said fitting and being exposed through said at least one slot, said length of tubing being made of silicone rubber, (iii) a silicone rubber glue, said silicone rubber glue being sandwiched between an exposed portion of said length of tubing and said medical catheter for bonding said length of tubing to said medical catheter, and (iv) a wire loop, said wire loop being secured to said front portion of said fitting and extending forwardly therefrom.

According to still a further aspect of the invention, there is provided a medical catheter assembly comprising (a) a medical catheter, said medical catheter being made of silicone rubber and having a proximal end, a distal end and a longitudinal bore; (b) an internal bolster, said internal bolster being disposed at said distal end of said medical catheter; (c) a connector, said connector being an elongated member having a front portion, a rear portion, and a longitudinal bore, said rear portion having at least one transversely extending opening, said rear portion of said connector being disposed within said proximal end of said medical catheter; and (e) a silicone rubber glue, said silicone rubber glue being deposited into said at least one transversely-extending opening in said rear portion of said connector and in contact with said medical catheter for bonding to said medical catheter.

According to still yet a further aspect of the invention, there is provided a medical catheter assembly, said medical catheter assembly comprising (a) a medical catheter, said medical catheter being made of silicone rubber and having a proximal end, a distal end and a longitudinal bore; (b) an internal bolster, said internal bolster being disposed at said distal end of said medical catheter; and (c) a fitting assembly, said fitting assembly comprising (i) a fitting, said fitting including a front portion and a rear portion, said front portion being shaped to serve as a dilator, said rear portion being disposed within said proximal end of said medical catheter and being shaped to include at least one transversely-extending opening, (ii) a silicone rubber glue, said silicone rubber glue being deposited into said at least one transversely-extending opening in said rear portion of said fitting and in contact with said medical catheter for bonding to said medical catheter, and (iii) a wire loop, said wire loop being secured to said front portion of said fitting and extending forwardly therefrom.

For purposes of the present specification and claims, various relational terms like "top," "bottom," "upper," "lower," "front," and "rear" are used to describe the present invention when said invention is positioned in a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIGS. 5(a) through 5(d) are rear, side, section, and perspective views, respectively, of the connector shown in FIG. 4;

FIGS. 7(a) through 7(d) are rear, section, and a pair of orthogonal side views, respectively, of the combination of the fitting and the wire loop shown in FIG. 6;

FIGS. 11(a) through 11(d) are rear, section, and a pair of orthogonal side views, respectively, of the connector shown in FIG. 10;

DETAILED DESCRIPTION OF PREFERRED EMBODIMENTS

Figure 1:
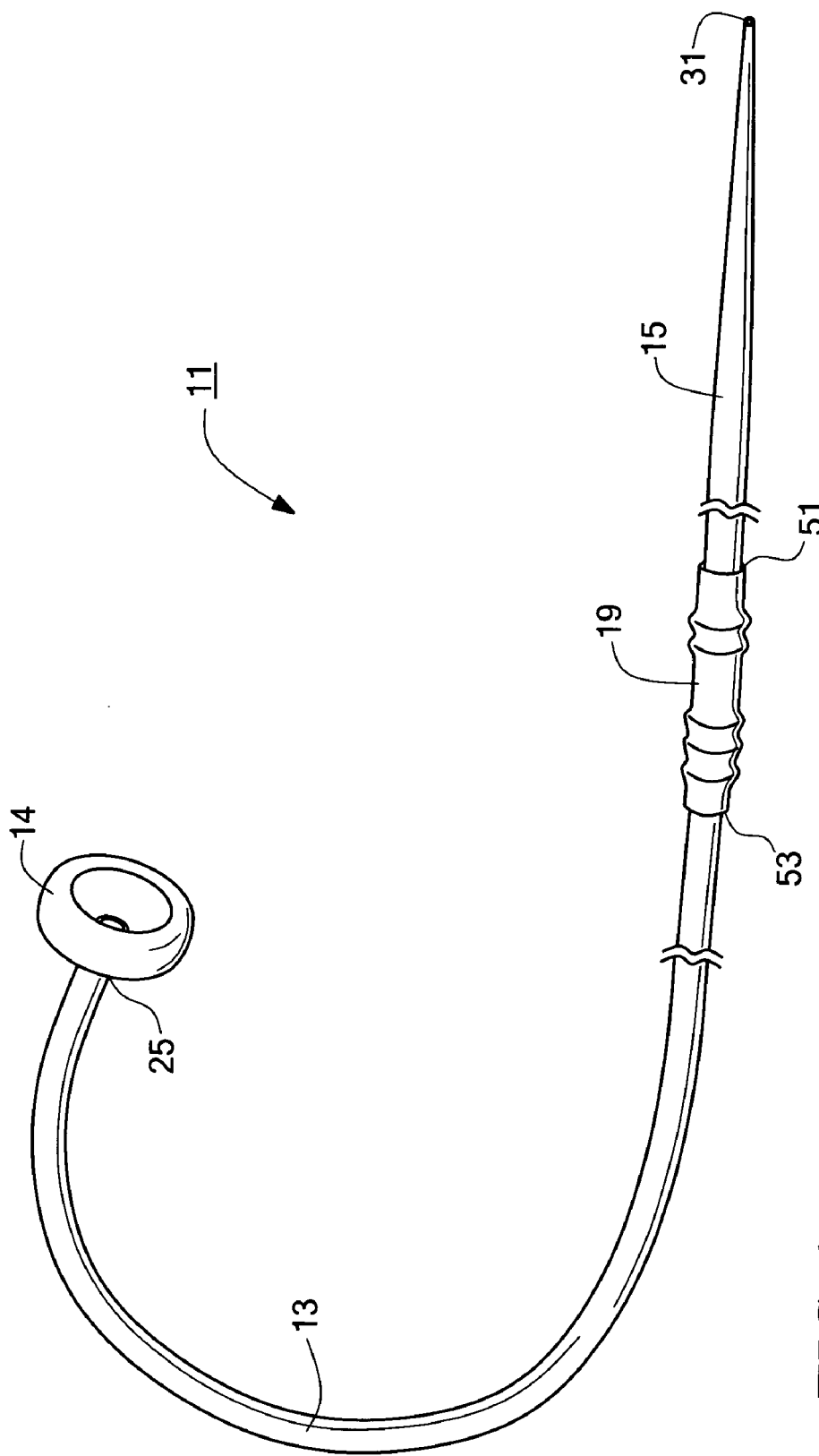
FIG. 1 is a fragmentary, perspective view of a conventional medical catheter assembly adapted for percutaneous endoscopic implantation in a patient using the push method.
Figure 2:
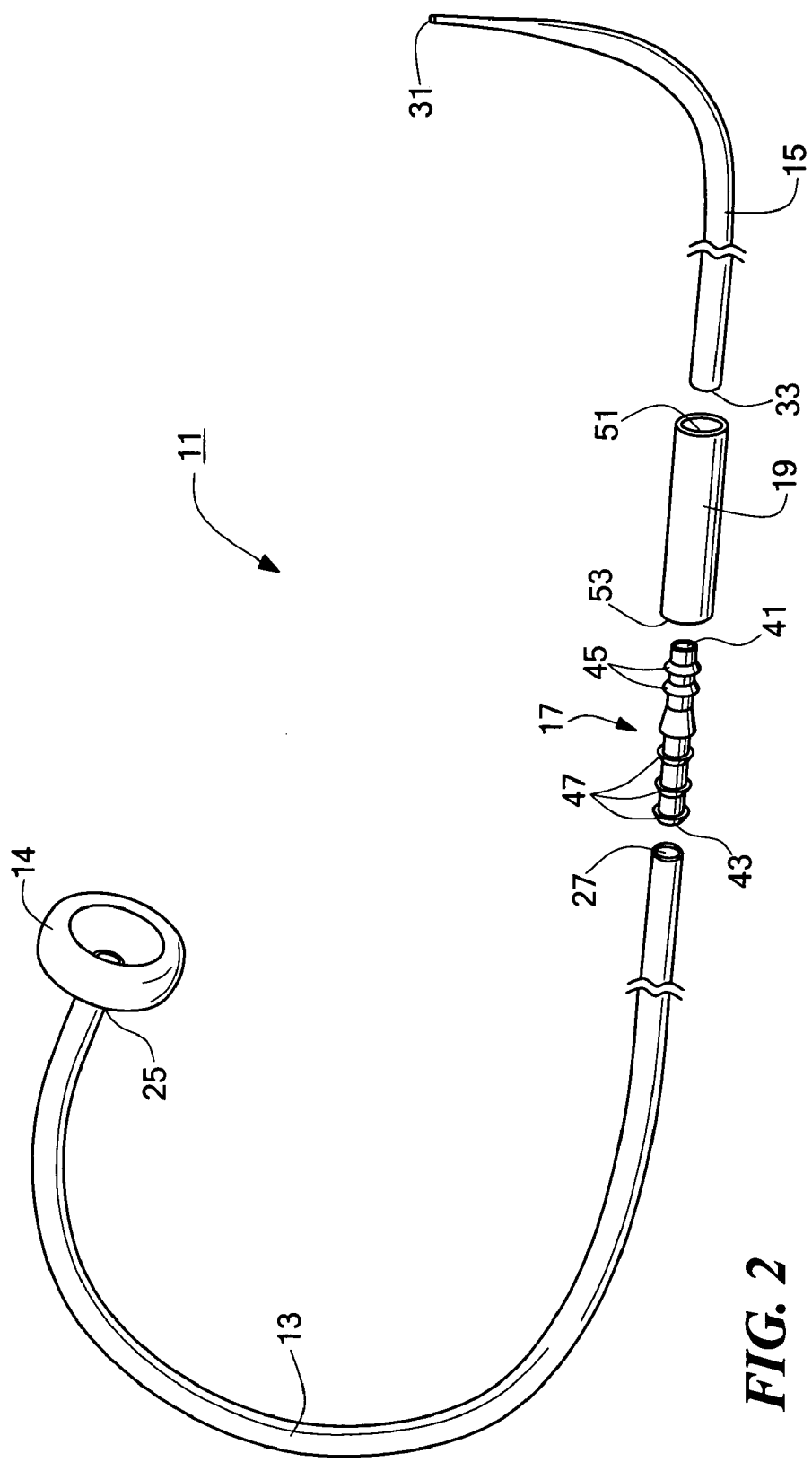
FIG. 2 is a fragmentary, exploded, perspective view of the conventional medical catheter assembly of FIG. 1 prior to the heat-shrinking of the short plastic tubing.

Referring now to FIGS. 1 and 2, there are shown fragmentary, perspective and fragmentary, exploded, perspective views, respectively, of a conventional medical catheter assembly adapted for percutaneous endoscopic implantation in a patient using the push method, said conventional medical catheter assembly being represented generally by reference numeral 11.

Assembly 11, which is shown prior to use on a patient, comprises a gastrostomy feeding tube 13, an internal bolster 14, a dilator 15, a connector 17 and a short length of tubing 19.

Tube 13, which is made of a soft, biocompatible, silicone rubber, is an elongated, cylindrical member shaped to include a trailing end 25 and a leading end 27. Internal bolster 14, which is also made of a soft, biocompatible, silicone rubber, is securely disposed at trailing end 25 of tube 13 and, in the present embodiment, forms a unitary structure therewith. A series of ruler markings (not shown) are printed on tube 13 and extend several inches from trailing end 25 in the direction of leading end 27 to facilitate the cutting of tube 13, once it has been implanted in a patient, to a desired length.

Dilator 15, which is made of a polyethylene having sufficient rigidity to open a stoma and sufficient flexibility to permit its being bent through a patient, is a tubular member having a leading end 31 and a trailing end 33. Dilator 15 is dimensioned to gradually increase in diameter over a length of several inches from leading end 31, which is sized to conform closely to a guidewire inserted thereinto, to trailing end 33, which is sized to approximate the dimensions of leading end 27 of tube 13.

Connector 17, which is made of a rigid plastic, is a unitary tubular member having a leading end 41 and a trailing end 43. Leading end 41, which is inserted into trailing end 33 of dilator 15, is shaped to include a plurality of barbs 45 for engaging dilator 15. Trailing end 43, which is inserted into leading end 27 of gastrostomy feeding tube 13, is shaped to include a plurality of barbs 47 for engaging tube 13.

Tubing 19, which is a unitary member made of a heat-shrinkable material, is shaped to include a leading end 51 inserted over trailing end 33 of dilator 15 (as well as over leading end 41 of connector 17) and a trailing end 53 inserted over leading end 27 of tube 13 (as well as over trailing end 43 of connector 17). As can be seen in FIG. 1, because tubing 19 is tightly fitted over tube 13, dilator 15, and connector 17, tubing 19 helps to soften the transition of outer dimensions among the various components.

However, as noted above, despite the reinforcement to the connection provided by tubing 19, assembly 11 often fails to withstand tensile forces in the range of about 17 pounds and, therefore, does not meet industry standards. In addition, the application of tubing 19 to its underlying components adds time and labor and, therefore, expense to the manufacture of assembly 11. Furthermore, tubing 19 adds to the cross-sectional profile of assembly 11, and there is a perception in the industry that ends 51 and 53 of tubing 19, which do not lie flush with dilator 15 or feeding tube 13, may snag tissue as assembly 11 winds its way through a patient.

Figure 3:
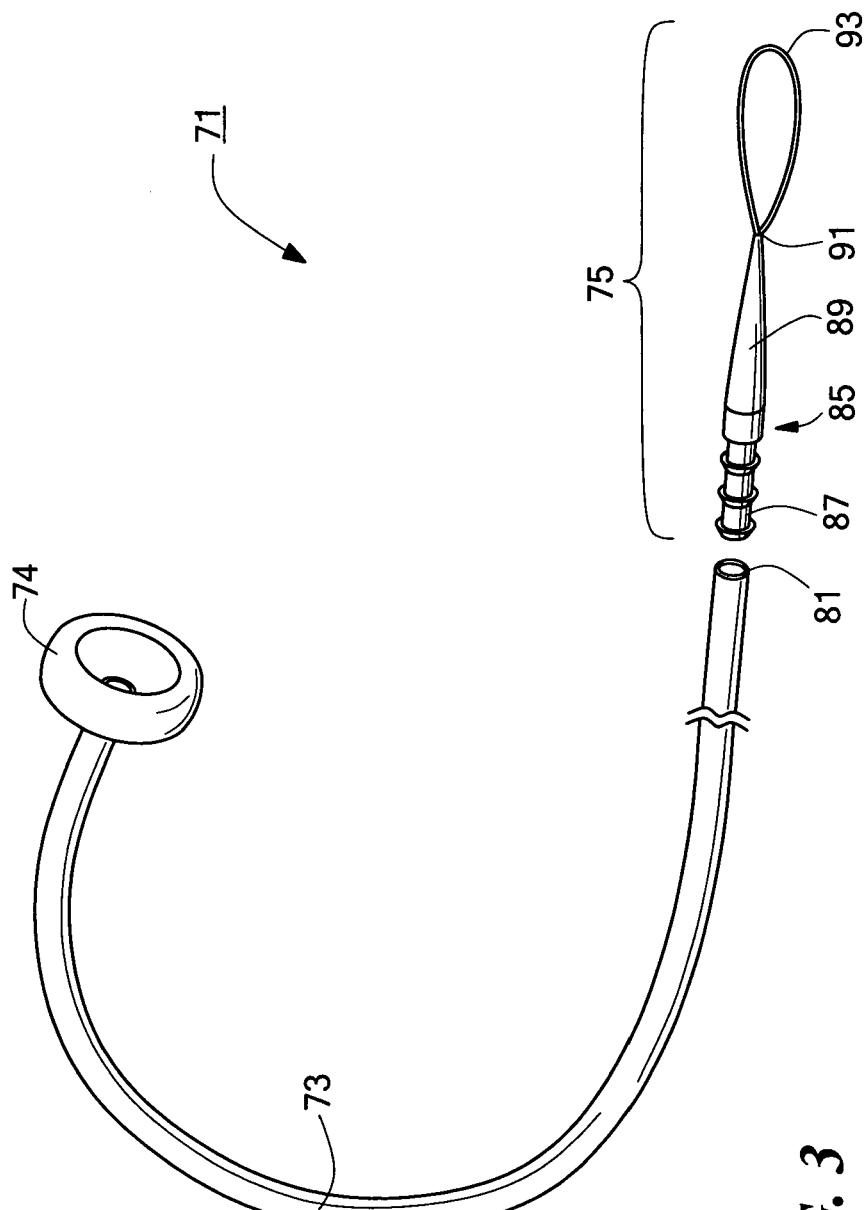
FIG. 3 is a fragmentary, partially exploded, perspective view of a conventional medical catheter assembly adapted for percutaneous endoscopic implantation in a patient using the pull method.

Referring now to FIG. 3, there is shown a fragmentary, partially exploded, perspective view of a conventional medical catheter assembly adapted for percutaneous endoscopic implantation in a patient using the pull method, said conventional medical catheter assembly being represented generally by reference numeral 71.

Assembly 71, which is shown prior to use on a patient, comprises a gastrostomy feeding tube 73, an internal bolster 74 and a fitting assembly 75.

Tube 73 and bolster 74 are indistinguishable in size, shape and composition from tube 13 and bolster 14, respectively, of assembly 11.

Fitting assembly 75 comprises a fitting 85. Fitting 85, which is made of a rigid plastic, is shaped to include a barbed rear portion 87 mounted within leading end 81 of tube 73 and a conical front portion 89 that serves as a dilator, front portion 89 tapering in diameter from a point proximate to leading end 81 of tube 73 to a front tip 91. A wire loop 93, which is adapted to be secured to the first end of a suture, is fixed (typically by insert-molding) to front tip 91.

Unfortunately, as noted above, assembly 71 often fails to withstand tensile forces in the range of about 17 pounds, with fitting 85 frequently being pulled out of tube 73.

Figure 4:
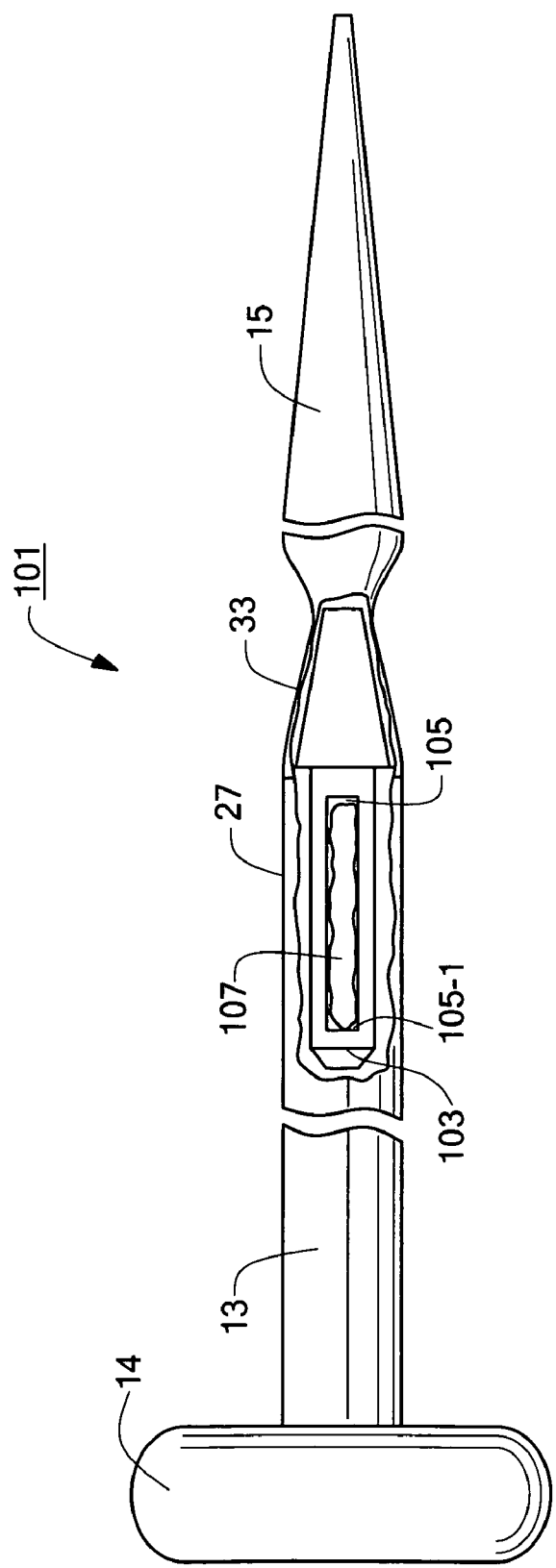
FIG. 4 is a fragmentary, side view, broken away in part, of a first embodiment of a medical catheter assembly constructed according to teachings of the present invention and adapted for percutaneous endoscopic implantation in a patient using the push method.

Referring now to FIG. 4, there is shown a fragmentary, side view, broken away in part, of a first embodiment of a medical catheter assembly constructed according to teachings of the present invention and adapted for percutaneous endoscopic implantation in a patient using the push method, said medical catheter assembly being represented generally by reference numeral 101.

Assembly 101, which is shown prior to use on a patient, is similar in many respects to assembly 11, assembly 101 likewise comprising a gastrostomy feeding tube 13, an internal bolster 14 and a dilator 15. Assembly 101 differs from assembly 11, however, in that assembly 101 does not include the combination of connector 17 and tubing 19 for interconnecting tube 13 and dilator 15. Instead, assembly 101 comprises, as a means for interconnecting tube 13 and dilator 15, the combination of a connector 103, a length of silicone tubing 105 mounted within connector 103, and a quantity of silicone glue 107 (e.g., Nusil's MED 4860) applied to the exposed portions of silicone tubing 105 within connector 103 for use in bonding tubing 105 to tube 13. For reasons to become apparent below, tubing 105 is appropriately dimensioned to receive a guidewire therethrough.

Referring now to FIGS. 5(a) through 5(d), there are shown various isolated views of connector 103. Connector 103, which is a unitary member preferably made of molded plastic, is shaped to include a rear portion 110 and a front portion 115. Rear portion 110, in turn, includes a rearward section 111 and a forward section 113. Rearward section 111, which is inserted into leading end 27 of tube 13, is frusto-conical in shape, tapering rearwardly in cross-sectional diameter from its front end 112. A centrally-disposed, longitudinal bore 117 is provided in rearward section 111, bore 117 being appropriately dimensioned to receive a guidewire therethrough.

Forward section 113, which is also inserted into leading end 27 of tube 13, is generally cylindrical in shape. A centrally-disposed, longitudinal bore 119 is provided in forward section 113, bore 119 being coaxial with bore 117 but larger in diameter than bore 117. A pair of longitudinally-extending slots 121-1 and 121-2 permitting access to bore 119 are provided on opposite sides of forward section 113, slots 121 and bore 119 forming a "cage-like" structure. As will be discussed below in greater detail, silicone tubing 105 may be inserted into forward section 113 through either of slots 121-1 and 121-2 and is securely received within bore 119, the rear end 105-1 of tubing 105 engaging front end 112 of rearward section 111.

Front portion 115, which is inserted into trailing end 33 of dilator 15, is frusto-conical in shape, tapering forwardly in cross-sectional diameter from its rear end 125. A centrally-disposed, longitudinal bore 127 is provided in front portion 115, bore 127 being aligned with and substantially equal in diameter to bore 119 of forward section 113. (The front end 127-1 of bore 127 is flared outwardly to a small extent to facilitate the insertion of a guidewire thereinto.)

Preferably, connector 103 is made of the same type of material as dilator 15. In this manner, front portion 115 may be secured to dilator 15 by spin-welding. Spin-welding is a preferred technique for bonding connector 103 to dilator 15 since spin-welding results in the effective fusing together of front portion 115 and dilator 15 for a very secure bond. If, however, front portion 115 cannot be spin-welded to dilator 15 (e.g., connector 103 and dilator 15 are made of different materials, the equipment needed for spin-welding is not available, etc.), one may modify front portion 115 and/or dilator 15 to include any well-known mechanical fastening mechanism (e.g., mating threads).

As can readily be appreciated, because silicone tubing 105 is bonded to tube 13 with a silicone glue 107, the strength of the bond between tube 105 and tube 13 is considerable. Moreover, because the rear end 105-1 of tubing 105 abuts the front end 112 of rear section 111 when a rearward force is applied to tubing 105, tubing 105 is able to remain seated within connector 103 despite considerable separation forces (in many instances approaching or exceeding industry minimum standards).

To assemble assembly 101, front portion 115 of connector 103 is inserted into trailing end 33 of dilator 15 and is spin-welded thereto. Next, tubing 105 is inserted into bore 119 through one of slots 121-1 and 121-2 of forward section 113, and rear portion 110 of connector 103 is then inserted into leading end 27 of tube 13. Then, using a needle and syringe (or like device), a quantity of silicone glue 107 is injected transversely through tube 13 and is deposited onto those surfaces of tube 105 that are left uncovered by slots 121. (Alternatively, instead of injecting silicone glue transversely through tube 13, one may choose not to insert forward section 113 completely into tube 13 and to inject the silicone glue over the exposed portions of tube 105 or may choose to pull tube 13 away from rear portion 110 and to inject the silicone glue directly onto the exposed portions of tube 105. Thereafter, leading end 27 of tube 13 is pulled over the remainder of forward section 113.) The assembly is then heated in an oven until the silicone glue 107 cures. Assembly 101 is then used in the same manner as assembly 11.

Figure 6:
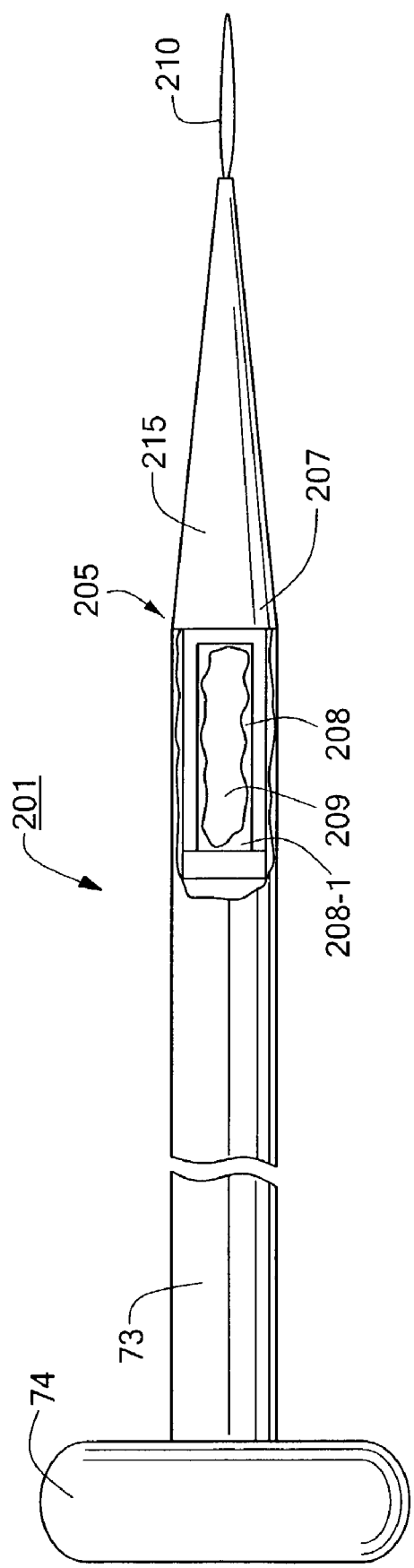
FIG. 6 is a fragmentary, side view, broken away in part, of a first embodiment of a medical catheter assembly constructed according to teachings of the present invention and adapted for percutaneous endoscopic implantation in a patient using the pull method.

Referring now to FIG. 6, there is shown a fragmentary, side view, broken away in part, of a first embodiment of a medical catheter assembly constructed according to teachings of the present invention and adapted for percutaneous endoscopic implantation in a patient using the pull method, said medical catheter assembly being represented generally by reference numeral 201.

Assembly 201, which is shown prior to use on a patient, is similar in many respects to assembly 71, assembly 201 likewise comprising a gastrostomy feeding tube 73 and an internal bolster 74. Assembly 201 differs, however, from assembly 71 in that assembly 201 does not include a fitting assembly 75. Instead, assembly 201 comprises a fitting assembly 205, fitting assembly 205 comprising a fitting 207, a length of silicone tubing 208, a quantity of silicone glue 209 applied to the exposed portions of tubing 208 within fitting 207, and a wire loop 210.

Referring now to FIGS. 7(a) through 7(d), there are shown various views of fitting 207 and wire loop 210 (tubing 208 and glue 209 not being shown). Fitting 207, which is similar in many respects to connector 103, is a unitary member shaped to include a rear portion 211 and a front portion 215. Rear portion 211, which is inserted into leading end 27 of tube 13, is cylindrical in shape. A centrally-disposed, longitudinal bore 219 is provided in rear portion 211. In addition, a pair of longitudinally-extending slots 221-1 and 221-2 permitting access to bore 219 are provided on opposite sides of rear portion 211, slots 221 and bore 219 forming a "cage-like" structure. As will be discussed below in greater detail, silicone tubing 208 is inserted into rear portion 211 through either of slots 221-1 and 221-2 and is received within bore 219, the rear end 208-1 of tubing 208 engaging rear wall 212 bounding bore 219. Front portion 215, which serves as a dilator, is substantially conical in shape, front portion 215 tapering forwardly in cross-sectional diameter from its rear end 225 to a point 226.

Preferably, fitting 207, which is made of a suitable plastic, is insert-molded around wire loop 210 to provide a secure connection therebetween.

To assemble assembly 201, tubing 208 is inserted into bore 219 of rear portion 211 through one of slots 221, and rear portion 211 of fitting 207 is inserted into leading end 81 of tube 73. Then, a quantity of silicone glue 209 is injected transversely through tube 73 and is deposited onto those surfaces of tube 208 that are left uncovered by slots 221. (Alternatively, instead of injecting silicone glue transversely through tube 73, one may choose not to insert rear portion 211 completely into tube 73 and to inject the silicone glue over the exposed portions of tube 208 or may choose to pull tube 73 away from rear portion 211 and to inject the silicone glue directly onto the exposed portions of tube 208. Thereafter, leading end 81 of tube 73 is pulled over the remainder of rear portion 211.) The assembly is then heated in an oven until the silicone glue 209 cures. Assembly 201 is then used in the same manner as assembly 71.

Figure 8:
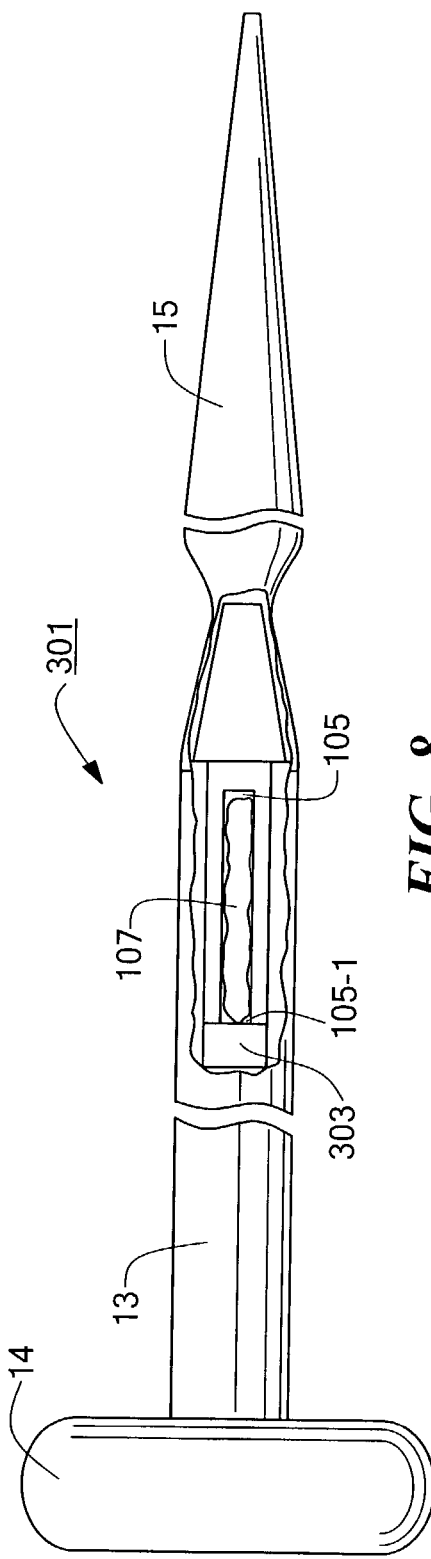
FIG. 8 is a fragmentary, side view, broken away in part, of a second embodiment of a medical catheter assembly constructed according to teachings of the present invention and adapted for percutaneous endoscopic implantation in a patient using the push method.
Figure 9D:
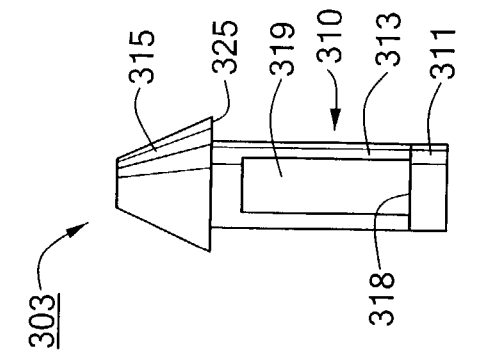
FIGS. 9(a) through 9(d) are rear, section, and a pair of orthogonal side views, respectively, of the connector shown in FIG. 8.
Figure 9C:
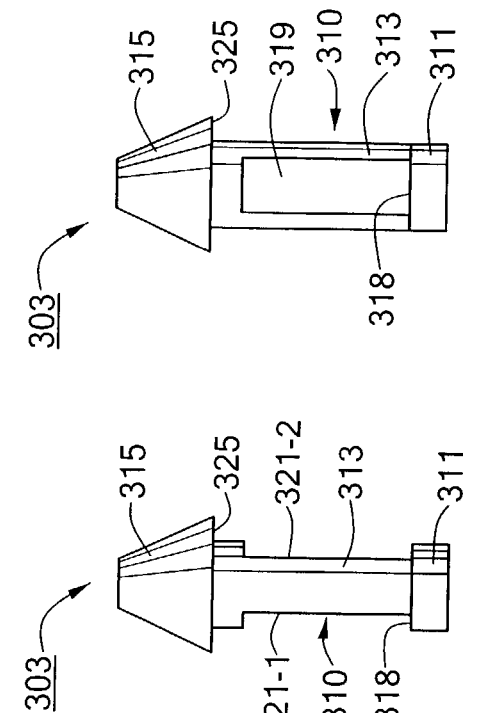
Figure 9B:
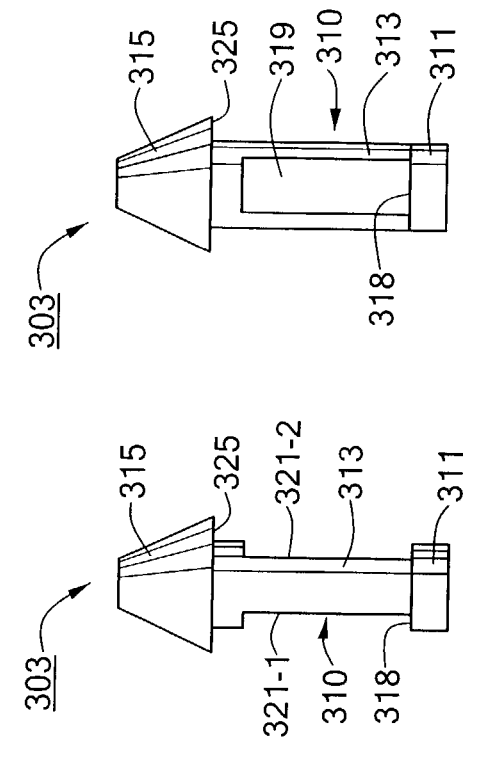
Figure 9A:
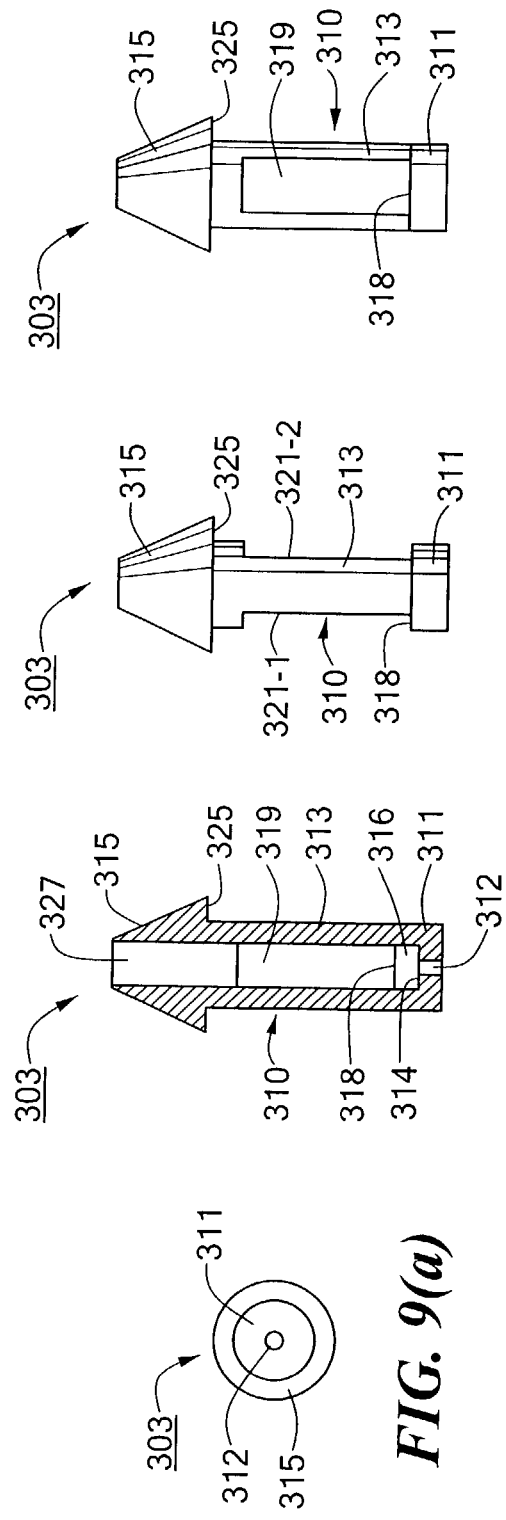

Referring now to FIG. 8, there is shown a fragmentary, side view, broken away in part, of a second embodiment of a medical catheter assembly constructed according to teachings of the present invention and adapted for percutaneous endoscopic implantation in a patient using the push method, said medical catheter assembly being represented generally by reference numeral 301.

Assembly 301, which is shown prior to use on a patient, is similar in most respects to assembly 101, the principal difference between the two assemblies being that assembly 301 comprises a connector 303, instead of connector 103.

Referring now to FIGS. 9(a) through 9(d), there are shown various isolated views of connector 303. Connector 303, which is a unitary member preferably made of molded plastic, is shaped to include a rear portion 310 and a front portion 315. Rear portion 310, in turn, comprises a rearward section 311 and a forward section 313. Rearward section 311, which is inserted into leading end 27 of tube 13, is cylindrical in shape and includes a rear wall 314. A centrally-disposed, smaller-diameter bore 312, which is appropriately dimensioned to receive a guidewire therethrough, extends through rear wall 314, and a centrally-disposed, larger-diameter bore 316, which is appropriately dimensioned to receive the rear portion of tube 105, extends longitudinally rearwardly from a front end 318 in rear section 311 and terminates at rear wall 314, bores 312 and 316 being in fluid communication with one another.

Forward section 313, which is also inserted into leading end 27 of tube 13, is generally cylindrical in shape and has the same outer diameter as rearward section 311. A centrally-disposed, longitudinal bore 319 is provided in forward section 313, bore 319 being coaxial with and equal in diameter to bore 316. A pair of longitudinally-extending slots 321-1 and 321-2 permitting access to bore 319 are provided on opposite sides of forward section 313. (In use, silicone tubing 105 is inserted through either of slots 321-1 and 321-2 and is received within bores 316 and 319, with the rear end 105-1 of tubing 105 engaging the rear end 314 of bore 316.)

Front portion 315, which is inserted into trailing end 33 of dilator 15, is frusto-conical in shape, tapering forwardly in cross-sectional diameter from its rear end 325. A centrally-disposed, longitudinal bore 327 is provided in front portion 315, bore 327 being aligned with and substantially equal in diameter to bore 319 of forward section 313.

Assembly 301 is assembled and used in substantially the same manner as assembly 101. One possible advantage of assembly 101 to assembly 301 is that it may be easier to mold connector 103 than to mold connector 303 since the molding of connector 303 requires the creation of bore 316, which, as an undercut, may require a snap-core or like device to be used during the molding process.

Figure 10:
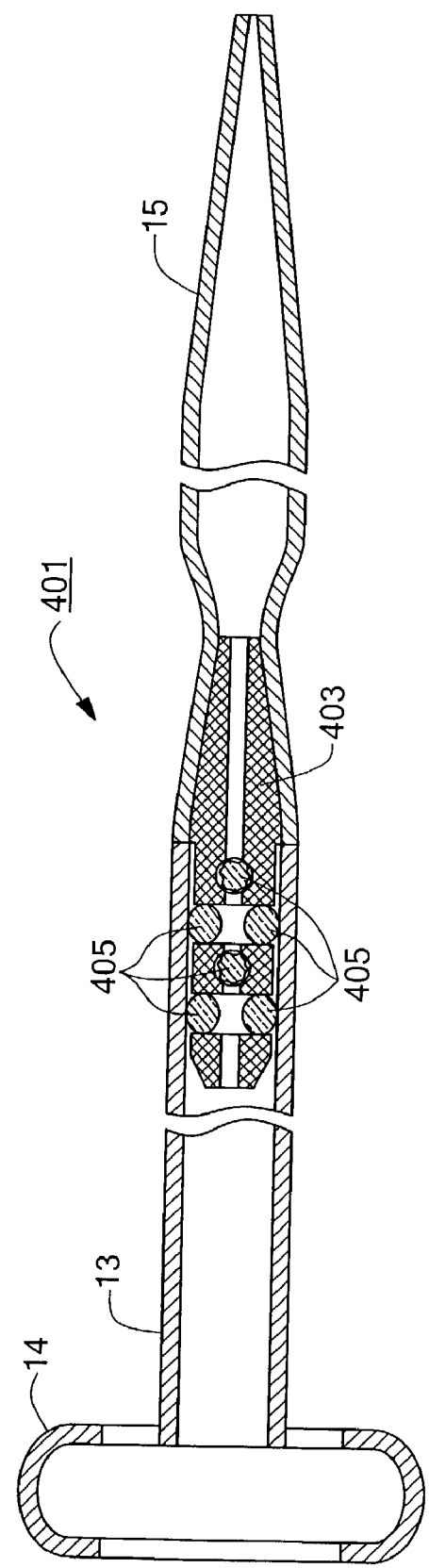
FIG. 10 is a fragmentary, section view of a third embodiment of a medical catheter assembly constructed according to the teachings of the present invention and adapted for percutaneous endoscopic implantation in a patient using the push method.

Referring now to FIG. 10, there is shown a fragmentary, section view of a third embodiment of a medical catheter assembly constructed according to the teachings of the present invention and adapted for percutaneous endoscopic implantation in a patient using the push method, said medical catheter assembly being represented generally by reference numeral 401.

Assembly 401, which is shown prior to use on a patient, is similar in many respects to assembly 101, the principal difference between the two assemblies being that assembly 401 does not include the combination of connector 103, tubing 105 and silicone glue 107 to interconnect tube 13 and dilator 15. Instead, assembly 401 comprises, as a means for interconnecting tube 13 and dilator 15, the combination of a connector 403 and a quantity of silicone glue 405 applied to connector 403 in the manner hereinafter described.

Referring now to FIGS. 11(a) through 11(d), there are shown various isolated views of connector 403. Connector 403, which is a unitary member preferably made of molded plastic, is shaped to include a front portion 409 and a rear portion 411. Front portion 409, which is inserted into the trailing end 33 of dilator 15, is generally frusto-conical in shape, tapering forwardly in cross-sectional diameter to facilitate its insertion into dilator 15 and to permit its being spin-welded to dilator 15. Rear portion 411, which is inserted into leading end 27 of tube 13, is generally cylindrical in shape, the rear end 417 of rear portion 411 tapering rearwardly in cross-sectional diameter to facilitate its insertion into leading end 27 of tube 13. A plurality of openings 419-1, 419-2, 419-3 and 419-4, the purpose of which will be described below, are provided in rear portion 411 and extend transversely through the longitudinal axis thereof. Openings 419-1 and 419-3 are parallel to one another, and openings 419-2 and 419-4 are parallel to one another, openings 419-1 and 419-3 extending perpendicularly relative to openings 419-2 and 419-4.

A centrally-disposed bore 421, which is appropriately dimensioned to receive a guidewire therethrough, extends the length of connector 403. The front end 423 of bore 421 is enlarged to facilitate the insertion of a guidewire To assemble assembly 401, front portion 409 of connector 403 is inserted into trailing end 33 of dilator 15 and is spin-welded thereto. Next, rear portion 411 of connector 403 is inserted into leading end 27 of tube 13. Next, a mandrel, preferably made of a metal or another like material that does not readily stick to silicone glue, is inserted from either tube 13 or dilator 15 into bore 421. Then, using a needle and syringe (or like device), silicone glue 405 is injected transversely through tube 13 and is used to fill to beyond capacity all of openings 419-1 through 419-4 until the excess glue from openings 419-1 through 419-4 contacts tube 13. (Alternatively, instead of injecting silicone glue transversely through tube 13, one may choose not to insert rear portion 411 completely into tube 13 and to inject the silicone glue directly into openings 419-1 through 419-4 or may choose to pull tube 13 away from rear portion 411 and to inject the silicone glue directly into openings 419-1 through 419-4. Thereafter, leading end 27 of tube 13 may be pulled over the remainder of rear portion 411.) The assembly is then heated in an oven until the silicone glue 405 cures, forming a secure bond to tube 13. The mandrel is then removed, and assembly 401 is used in the same manner as assembly 11.

It should be noted that, because openings 419-1 through 419-4 have a certain degree of concavity at their ends, connector 403 effectively forms the female analog of a barb, without having the undesired effect of causing tube 13 to become bloused around connector 403.

It should also be noted that, although openings 419-1 through 419-4 extend transversely entirely through rear portion 411 in the present embodiment, connector 403 could be modified so that one or more of openings 419-1 through 419-4 extend transversely only partially through rear portion 411 (for example, terminating prior to intersecting with bore 421). Moreover, it should be noted that the number of openings 419 in connector 403, the shape of openings 419, and their relative orientations are illustrative only.

Figure 12:
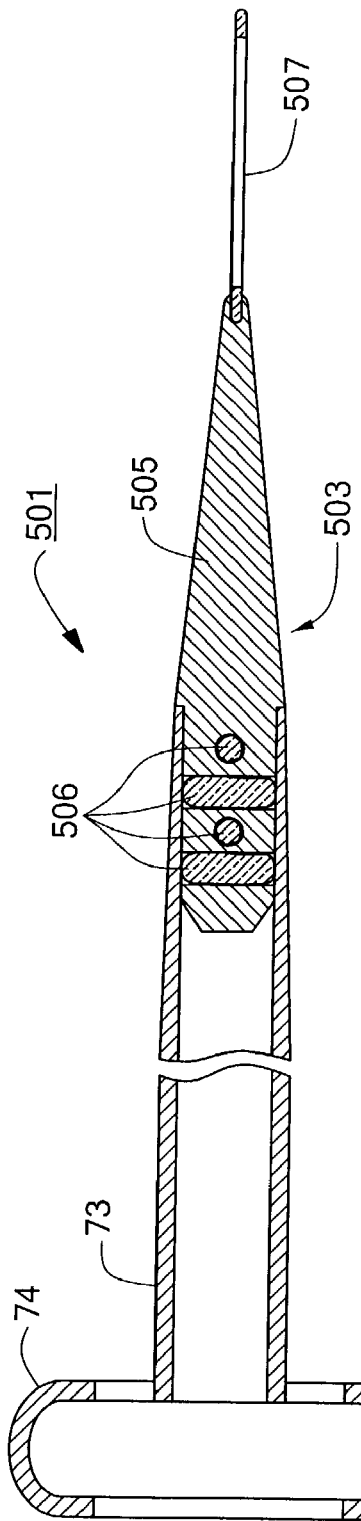
FIG. 12 is a fragmentary, section view of a second embodiment of a medical catheter assembly constructed according to the teachings of the present invention and adapted for percutaneous endoscopic implantation in a patient using the pull method.
Figure 13A:
FIGS. 13(a) through 13(d) are rear, section, and a pair of orthogonal side views, respectively, of the combination of the fitting and the wire loop shown in FIG. 12.
Figure 13B:
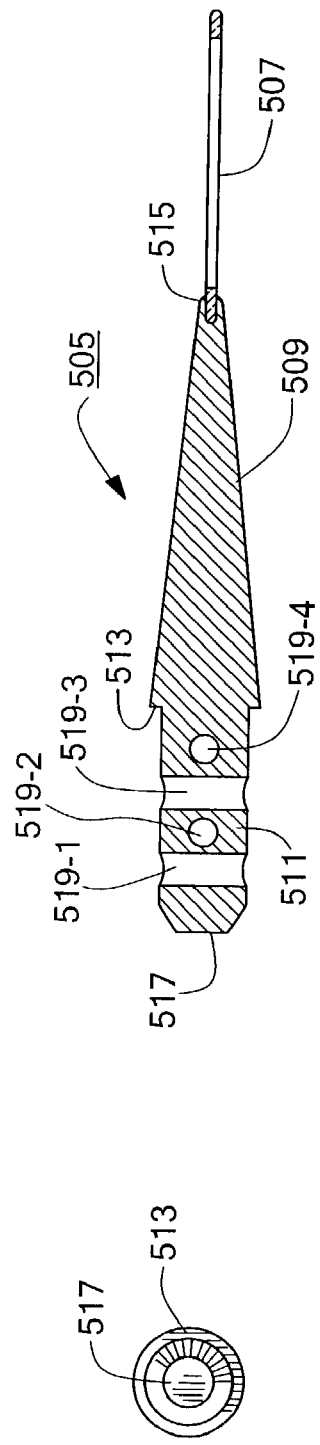
Figure 13C:
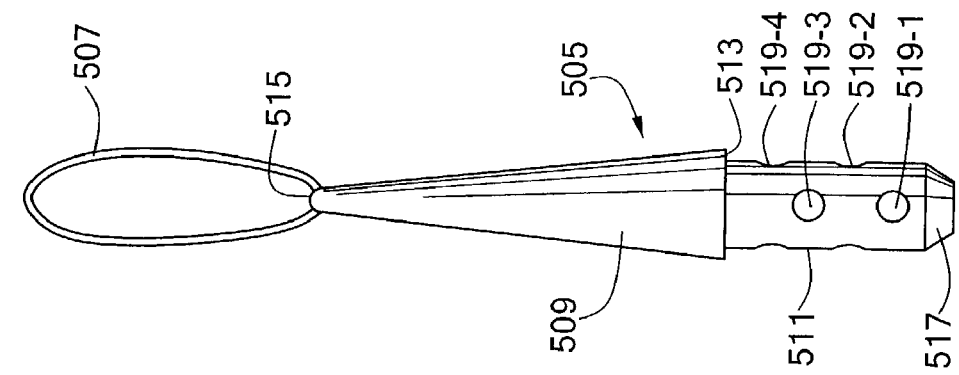
Figure 13D:
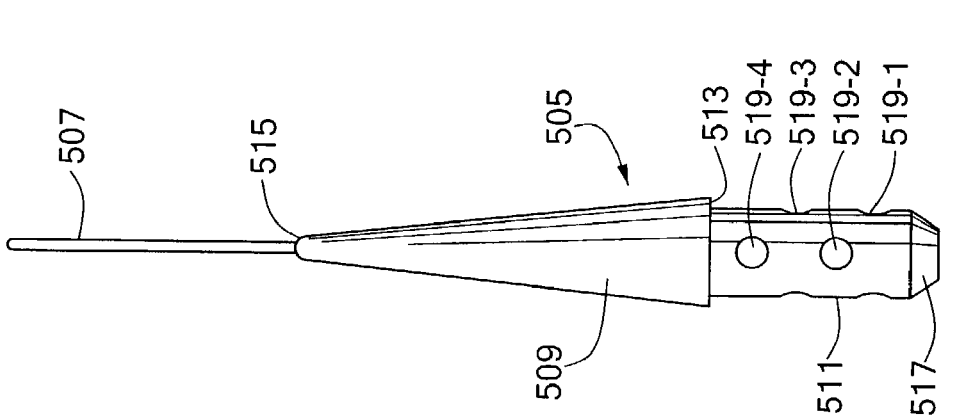

Referring now to FIG. 12, there is a fragmentary, side view, broken away in part, of a second embodiment of a medical catheter assembly constructed according to the teachings of the present invention and adapted for percutaneous endoscopic implantation in a patient using the pull method, said medical catheter assembly being represented generally by reference numeral 501.

Assembly 501, which is shown prior to use on a patient, is similar in many respects to assembly 71, assembly 501 likewise comprising a gastrostomy feeding tube 73 and an internal bolster 74. Assembly 501 differs, however, from assembly 71 in that assembly 501 does not include a fitting assembly 75. Instead, assembly 501 comprises a fitting assembly 503, fitting assembly 503 comprising a fitting 505, a quantity of silicone glue 506 applied to fitting 505 in the manner hereinafter described, and a wire loop 507.

Referring now to FIGS. 13(a) through 13(d), there are shown various views of fitting 505 and wire loop 507 (glue 506 not being shown). Fitting 505, which is similar in many respects to connector 403, is a unitary member, preferably made of molded plastic, that is shaped to include a front portion 509 and a rear portion 511. Front portion 509, which serves as a dilator, is generally conical in shape, tapering forwardly in cross-sectional diameter from its rear end 513 to a tip 515. Rear portion 511, which is inserted into leading end 27 of tube 13, is generally cylindrical in shape, the rear end 517 of rear portion 511 tapering rearwardly in cross-sectional diameter to facilitate its insertion into leading end 27 of tube 13. A plurality of openings 519-1, 519-2, 519-3 and 519-4, the purpose of which will be described below, are provided in rear portion 511 and extend transversely through the longitudinal axis thereof. Openings 519-1 and 519-3 are parallel to one another, and openings 519-2 and 519-4 are parallel to one another, openings 519-1 and 519-3 extending perpendicularly relative to openings 519-2 and 519-4.

Preferably, fitting 505, which is made of a suitable plastic, is insert-molded around wire loop 507 to provide a secure connection therebetween.

To assemble assembly 501, rear portion 511 of fitting 505 is inserted into leading end 27 of tube 13. Then, using a needle and syringe (or like device), silicone glue 506 is injected transversely through tube 13 and is used to fill to beyond capacity all of openings 519-1 through 519-4 until the excess glue 506 from openings 519-1 through 519-4 contacts tube 13. (Alternatively, instead of injecting silicone glue transversely through tube 13, one may choose not to insert rear portion 511 completely into tube 13 and to inject the silicone glue directly into openings 519-1 through 519-4 or may choose to pull tube 13 away from rear portion 511 and to inject the silicone glue directly into openings 519-1 through 519-4. Thereafter, leading end 27 of tube 13 may be pulled over the uncovered portion of rear portion 511.) The assembly is then heated in an oven until the silicone glue 506 cures, forming a secure bond to tube 13. Assembly 501 is used in the same manner as assembly 11.

It should be noted that, although openings 519-1 through 519-4 extend entirely through rear portion 511 in the present embodiment, fitting 505 could be modified so that one or more of openings 519-1 through 519-4 extend only partially through rear portion 511. Moreover, it should be noted that the number of openings 519 in fitting 505, the shape of openings 519, and their relative orientations are illustrative only.

It should also be noted that, although the assemblies of the present invention have been described in the context of implanting tubes as part of percutaneous endoscopic gastrostomies, the present assemblies could also be used to implant catheters as part of any number of other medical procedures including, but not limited to, percutaneous endoscopic jejunostomies.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A medical catheter assembly comprising:
   (a) a medical catheter, said medical catheter being made of silicone rubber and having a proximal end, a distal end and a longitudinal bore;
   (b) an internal bolster, said internal bolster being disposed at said distal end of said medical catheter;
   (c) a connector, said connector being an elongated member having a front portion, a rear portion, and a longitudinal bore, said rear portion having at least one slot providing side access to said longitudinal bore, said rear portion of said connector being disposed within said proximal end of said medical catheter;
   (d) a length of tubing, said length of tubing being disposed within said longitudinal bore of said connector and being exposed through said at least one slot, said length of tubing being hollow and made of silicone rubber; and
   (e) a silicone rubber glue, said silicone rubber glue being sandwiched between an exposed portion of said length of tubing and said medical catheter for bonding said length of tubing to said medical catheter.

2. The medical catheter assembly as claimed in claim 1 further comprising a dilator, said dilator having a proximal end, a distal end and a longitudinal bore, said front portion of said connector being securely disposed within said distal end of said dilator.

3. The medical catheter assembly as claimed in claim 2 wherein said medical catheter is a gastrostomy feeding tube.

4. The medical catheter assembly as claimed in claim 1 wherein said medical catheter and said internal bolster form a unitary structure.

5. The medical catheter assembly as claimed in claim 2 wherein said connector is secured to said dilator by spin-welding.

6. The medical catheter assembly as claimed in claim 5 wherein each of said connector and said dilator is made of polyethylene.

7. The medical catheter assembly as claimed in claim 1 wherein said rear portion of said connector is shaped to include a rearward section and a forward section, said rearward section being frusto-conical in shape and tapering rearwardly, said forward section being cylindrical in shape and having a pair of opposing slots providing access to said longitudinal bore, and wherein said front portion of said connector is frusto-conical in shape and tapers forwardly.

8. A medical catheter assembly comprising:
   (a) a medical catheter, said medical catheter being made of silicone rubber and having a proximal end, a distal end and a longitudinal bore;
   (b) an internal bolster, said internal bolster being disposed at said distal end of said medical catheter;
   (c) a connector, said connector comprising a front portion and a rear portion, said rear portion being disposed within said proximal end of said medical catheter and being shaped to include a cavity, said cavity being accessible from a side opening in said rear portion;
   (d) a length of tubing, said length of tubing being disposed within said cavity of said connector and being exposed through said side opening, said length of tubing being hollow and made of silicone rubber; and
   (e) a silicone rubber glue, said silicone rubber glue being sandwiched between an exposed portion of said length of tubing and said medical catheter for bonding said length of tubing to said medical catheter.

9. The medical catheter assembly as claimed in claim 8 further comprising a dilator, said dilator having a proximal end, a distal end and a longitudinal bore, said front portion of said connector being securely disposed within said distal end of said dilator.

* * * * *